United States Patent [19]

Ehrenkranz

[11] Patent Number: 5,679,577
[45] Date of Patent: Oct. 21, 1997

[54] SYSTEM FOR VERIFYING THE AUTHENTICITY OF A URINE SPECIMEN UTILIZING LEVELS OF DISSOLVED GASES

[76] Inventor: Joel R. L. Ehrenkranz, Millbrook Rd., New Vernon, N.J. 07976

[21] Appl. No.: 681,076

[22] Filed: Jul. 22, 1996

Related U.S. Application Data

[63] Continuation of Ser. No. 91,125, Jul. 14, 1993, abandoned.
[51] Int. Cl.⁶ .................................................. G01N 33/48
[52] U.S. Cl. ....................... 436/133; 436/136; 436/901
[58] Field of Search .......................... 422/68.1, 82.13; 436/68, 136, 901, 133, 183

[56] References Cited

U.S. PATENT DOCUMENTS

| | | | |
|---|---|---|---|
| 4,215,197 | 7/1980 | Tarbutton | 435/18 |
| 4,299,794 | 11/1981 | Kelley et al. | 422/68 |
| 5,179,027 | 1/1993 | Fisher | 436/56 |
| 5,223,221 | 6/1993 | Copelan | 422/61 |

OTHER PUBLICATIONS

Arruda et. al. "Kidney International" 1977 pp. 307–317.
Stinebaugh et al. "Kidney Internation" 1981 pp. 1–7.
Duboso et al. "Journal Clinical Investigation" p. 85 pp. 1116–1123.
Schrier et al. "Diseases of the Kidney" 1993 p. 2678.

*Primary Examiner*—Jeffrey Snay
*Attorney, Agent, or Firm*—Crummy, Del Deo, Dolan, Griffinger & Vecchione

[57] ABSTRACT

A method for making measurements of the $O_2$ and $CO_2$ dissolved in a urine sample to determine the identity and the age of the specimen.

10 Claims, 4 Drawing Sheets ns of $O_2$ and $CO_2$ in a sample can also be used to screen
SYSTEM FOR VERIFYING THE AUTHENTICITY OF A URINE SPECIMEN UTILIZING LEVELS OF DISSOLVED GASES This application is a continuation of application Ser. No. 08/091,125 filed Jul. 14,1993, now abandoned.

BACKGROUND OF THE INVENTION

1. Field of the Invention

This invention relates to a method for determining the authenticity of a urine specimen by measuring the age of the sample and by chemical screening of false samples utilizing $CO_2$ and $O_2$ levels in solution.

2. Description of the Prior Art

Documenting a specimen's authenticity is today a routine part of many urine-based diagnostic studies. Urine testing is relatively easy to administer, provides accurate results when specimen integrity is ensured and is the test method of choice where there is a need to avoid more invasive procedures. Urine tests particularly susceptible to tampering include those used in the diagnosis of diabetes, pregnancy, substance abuse, and in the course of life insurance and pre-employment testing.

At times a patient may offer a bogus urine specimen to avoid certain consequences, such as a positive indication of substance abuse. The current standard method for detecting such attempts is to document urine specimen authenticity by taking a measurement of the urine temperature at the time of voiding. Temperatures outside a pre-established range are presumed not to be valid samples.

Unfortunately, the practice of artificially warming a bogus specimen to maintain or place its temperature within the established range is becoming a common practice, particularly when tests are being made to show evidence of substance abuse. For example, it was reported at a nuclear power facility in Maryland, employees selected at random for drug testing, heated "clean" urine samples in a microwave oven en route to the test and monitored the temperature of the surrogate urine with a portable thermometer to insure that the sample fell within the established range.

In addition to temperature measurements, efforts to control sample tampering have included measurement of creatinine, chloride, pH and specific gravity. These tests offer little practical value in establishing whether or not a sample is authentic. Direct observation of a subject, aside from the argument that it is direct abridgement of an individual's right to privacy, has been shown to be unreliable and degrading to all parties involved.

3. SUMMARY OF THE INVENTION

This invention concerns a new diagnostic test run on a urine specimen which can authenticate the specimen by determining its age. It consists of the measurement of the partial pressure of dissolved oxygen ($O_2$) and/or carbon dioxide ($CO_2$) in urine to establish either the absolute levels of $O_2$ or $CO_2$ in the specimen, or the rate of change of the $O_2$ and $CO_2$ concentrations in the specimen. Either of these measurements can be used to determine the time which has elapsed since a measured specimen left the body. In combination, these measurements can accurately determine age within acceptable statistical tolerances.

Elapsed time since generating a specimen is a function of the concentrations of $O_2$ and $CO_2$ in solution; and the rate of change of those concentrations in the tested sample.

Within a pre-determined range of limits the concentrations of $O_2$ and $CO_2$ in a sample can also be used to screen bogus substituted liquids, such as water and certain sodas, from true urine samples.

Aside from determining the age of a urine sample, the absolute level of $O_2$ and $CO_2$ concentrations in a urine specimen also depicts a range of biological variability which demonstrates that these two metabolic products are useful in other ways for diagnostic purposes. These would include diseases related to perturbation of metabolic function that result in altered $CO_2$ levels (e.g. renal disease, endocrine disease, shock) and diseases associated with oxygenation and ventilation, such as pulmonary, cardiac, and neuromuscular disorders. Accordingly, this novel diagnostic urine test is a viable and non-invasive alternative for monitoring blood gas (i.e. $O_2$ and $CO_2$) concentrations.

Additionally, certain other tests, e.g. glucose or potassium measurements, which ordinarily lose precision as a result of specimen aging can benefit from this novel diagnostic test. If such results are artefactually abnormal due to aging, and not intrinsically abnormal, this fact can be established through measurements of the $O_2$ and $CO_2$ concentrations in the specimen, and thereby validate the original test.

These and other objects and advantages of this novel testing, screening and diagnostic procedure will be appreciated from a consideration of the drawing and the teaching in the Description Of The Preferred Embodiments to follow.

4. BRIEF DESCRIPTION OF THE DRAWING

FIG.'s 6–8 are graphic displays of the change in gas concentrations of $O_2$ and $CO_2$ (referred to as $PO_2$ and $PCO_2$) in a sealed screw top container, and FIG.'s 9–11 are graphic displays of the change in gas concentrations of $O_2$ and $CO_2$ (referred to as $PO_2$ and $PCO_2$) in a screw top container with mineral oil.

5. DESCRIPTION OF THE PREFERRED EMBODIMENTS

To demonstrate the validity and practicality of urinary $O_2$ and $CO_2$ measurement as a diagnostic test, each experiment was performed in triplicate. Fresh urine samples were obtained from three healthy adult males. The $O_2$ and $CO_2$ concentrations were measured in unsealed open containers with a Radiometer Copenhager ABL 330 semi-automated clinical blood gas analyzer or Instrumentation Laboratory Model 1312 Blood Gas Manager. Each time point determination was corrected for specimen temperature at the time of gas analyses. The results of these measurements are displayed on FIGS. 1, 2 and 3.

Figure 1:
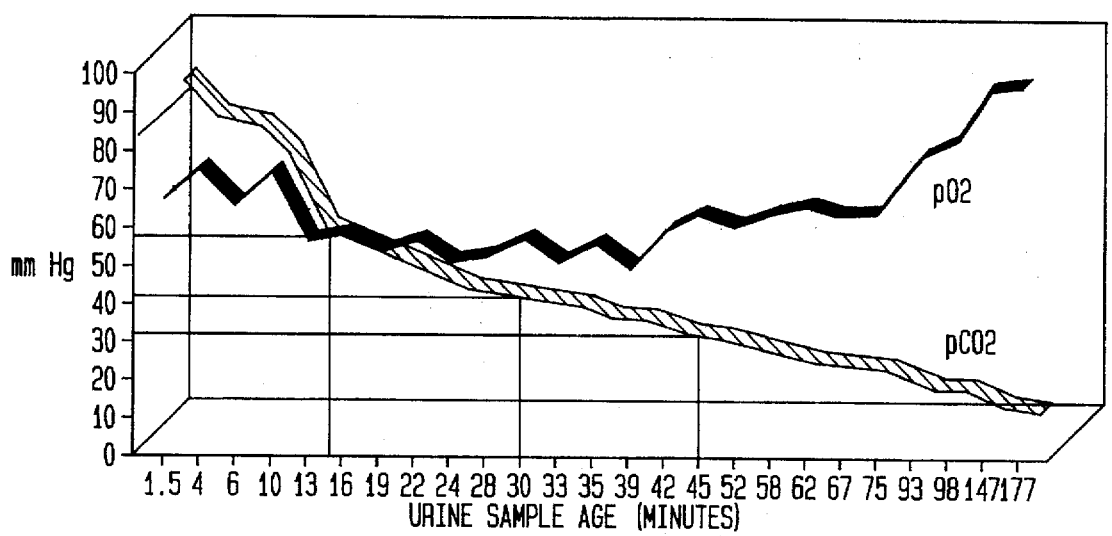
FIG. 1 is graphic display of measurements of $O_2$ and $CO_2$ showing changes in concentration levels over time in a first male subject urine specimen.

The data shown in FIG. 1 is based upon the following set of readings:

| time (min.) | O₂ mmHg | CO₂ mmHg |
| --- | --- | --- |
| 1.5 | 63.1 | 87.6 |
| 4 | 70.8 | 78.5 |
| 6 | 61.8 | 76.7 |
| 10 | 69.9 | 69.3 |
| 13 | 53.6 | 51.3 |
| 16 | 54.4 | 46.9 |
| 19 | 50.9 | 43.2 |
| 22 | 53.8 | 40 |
| 24 | 48.3 | 36.6 |
| 28 | 50.5 | 34.2 |
| 30 | 54.3 | 32.8 |
| 33 | 48.1 | 32.7 |
| 35 | 53.1 | 29.7 |
| 39 | 46.4 | 29.2 |
| 42 | 56.4 | 25.5 |
| 45 | 60.5 | 20.2 |
| 52 | 57.3 | 22.3 |
| 58 | 60.5 | 20.2 |
| 62 | 62.6 | 18.7 |
| 67 | 60 | 17.7 |
| 75 | 60.7 | 16.2 |
| 93 | 72.9 | 12.4 |
| 98 | 76.3 | 11.8 |
| 147 | 91.3 | 7.9 |
| 177 | 91.6 | 6.4 |

Figure 2:
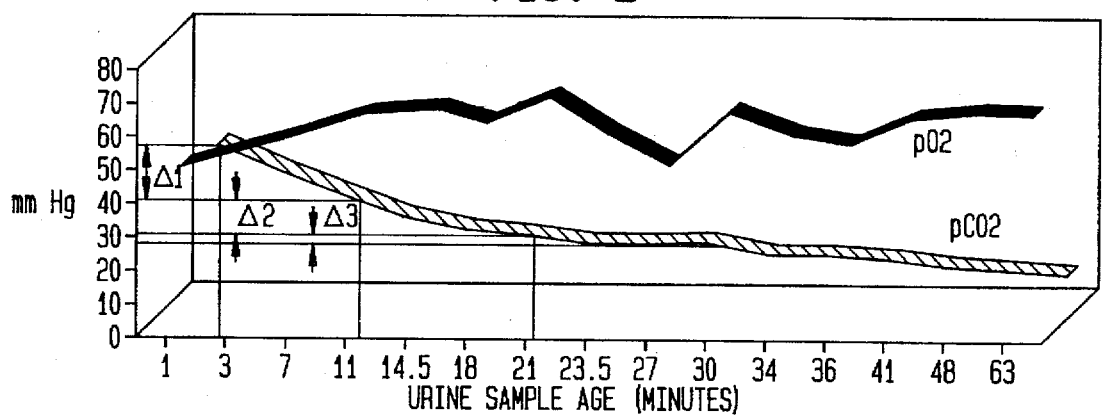
FIG. 2 is another graphic display of $O_2$ and $CO_2$ measurements showing changes in concentration levels over time for a second male subject urine specimen.

The data graphically depicted in FIG. 2 is based on the following measurements of $O_2$ and $CO_2$.

| time (min.) | O₂ mmHg | CO₂ mmHg |
| --- | --- | --- |
| 1 | 47.3 | 45.4 |
| 3 | 52.8 | 37.8 |
| 7 | 57.9 | 31.1 |
| 11 | 64.6 | 25.1 |
| 14.5 | 65.1 | 21.7 |
| 18 | 61.6 | 20.2 |
| 21 | 69.6 | 17.8 |
| 23.5 | 59.4 | 17.7 |
| 27 | 49.2 | 18.3 |
| 30 | 65.6 | 14.9 |
| 34 | 59.4 | 14.6 |
| 36 | 55.7 | 14.5 |
| 41 | 64 | 12 |
| 48 | 65.9 | 10.7 |
| 63 | 65.6 | 9.7 |

Figure 3:
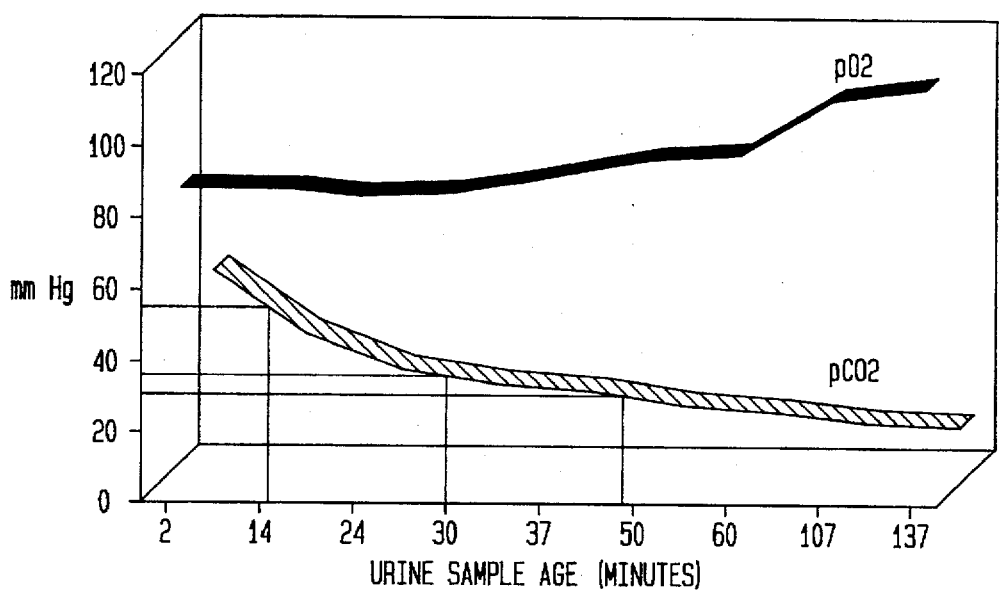
FIG. 3 is a third graphic display of measurements of $O_2$ and $CO_2$ showing changes in concentration levels over time for a third male subject urine specimen.

Finally, FIG. 3, depicts graphically the following set of measurements:

| time (min.) | O₂ mmHg | CO₂ mmHg |
| --- | --- | --- |
| 2 | 82.5 | 48.1 |
| 14 | 83.2 | 31.2 |
| 24 | 81.4 | 21.2 |
| 30 | 82.8 | 17.5 |
| 37 | 87.1 | 15.5 |
| 50 | 91.7 | 11.9 |
| 60 | 94.1 | 9.7 |
| 107 | 109.1 | 6.6 |
| 137 | 112.9 | 5.4 |

In every instance the concentration of $CO_2$ fell and $O_2$ rose as the sample was allowed to stand uncovered at room temperature under normal atmospheric conditions. Equilibrium (not shown on FIGS. 1, 2 and 3) was reached at a point where the partial pressure of the concentrations of $CO_2$ or $O_2$ equilibrated with atmospheric concentrations. $CO_2$ in a gaseous form was being liberated and $O_2$ was going into solution from the surrounding area. FIGS. 1-3 show that the partial pressures of the concentration measurements of $O_2$ and $CO_2$ ("also referred to as $PO_2$ and $PCO_2$") in a urine sample change dramatically with time and, in fact the concentration of $CO_2$ was reduced to less than half its original value after the first hour elapsed in all three samples, and after the second hour the partial pressure measurements of $O_2$ in the urine samples were significantly increased.

The rate of change in concentrations of $CO_2$ in a specimen can be used to accurately indicate the shorter intervals in the aging cycle. As shown in FIGS. 1-3 within the first 15 minutes following generation of a sample the concentration levels of $CO_2$ falls nearly one-third of its original value. In the next 15 minute interval the concentration level of $CO_2$ changes by approximately one-sixth of its value and in the third 15 minute interval the concentration change in $CO_2$ is one-twelfth of its value. These changes are depicted graphically in FIG. 2 as $\Delta_1$, $\Delta_2$ and $\Delta_3$ respectively. As can be seen the change in concentration levels of $CO_2$ can be plotted so that any specimen can be measured at pre-determined time intervals (e.g.; 15 minute intervals) to determine the delta, or rate of change, in concentration of $CO_2$ in the specimen. The delta, or rate of change, can be compared to pre-determined rates to indicate accurately the interval since the sample was generated, i.e. its age.

Figure 4:
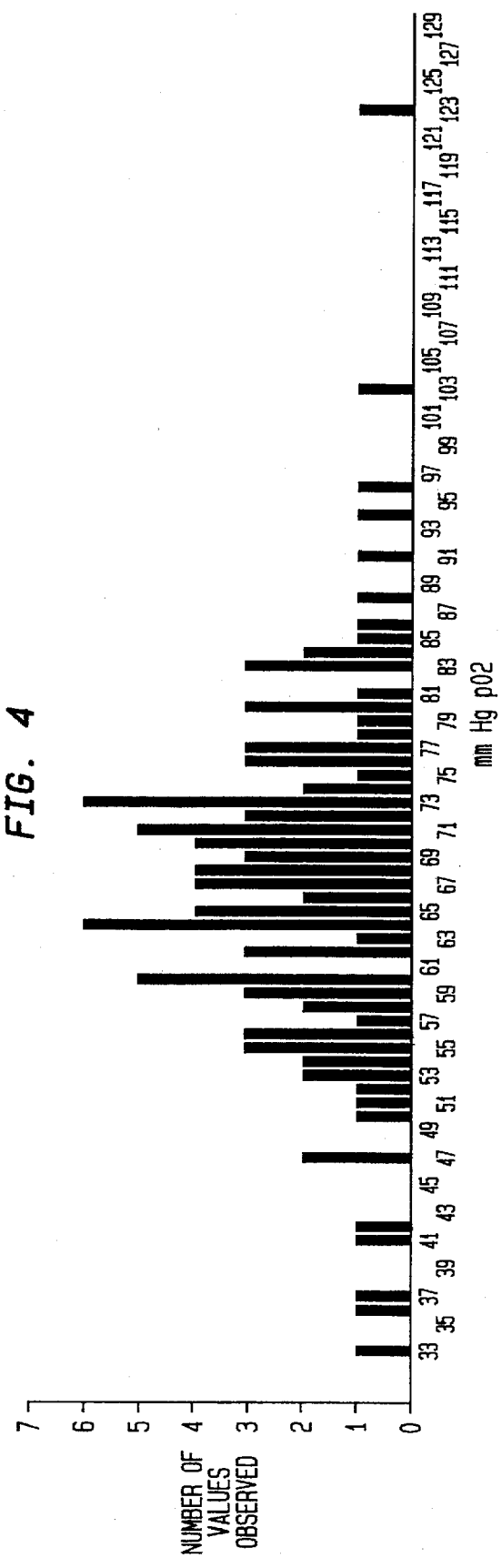
FIG. 4 is a bar graph display of the range of concentration of $O_2$ measurements in one hundred and four urine samples depicting the variations possible four minutes after the sample is given.
Figure 5:
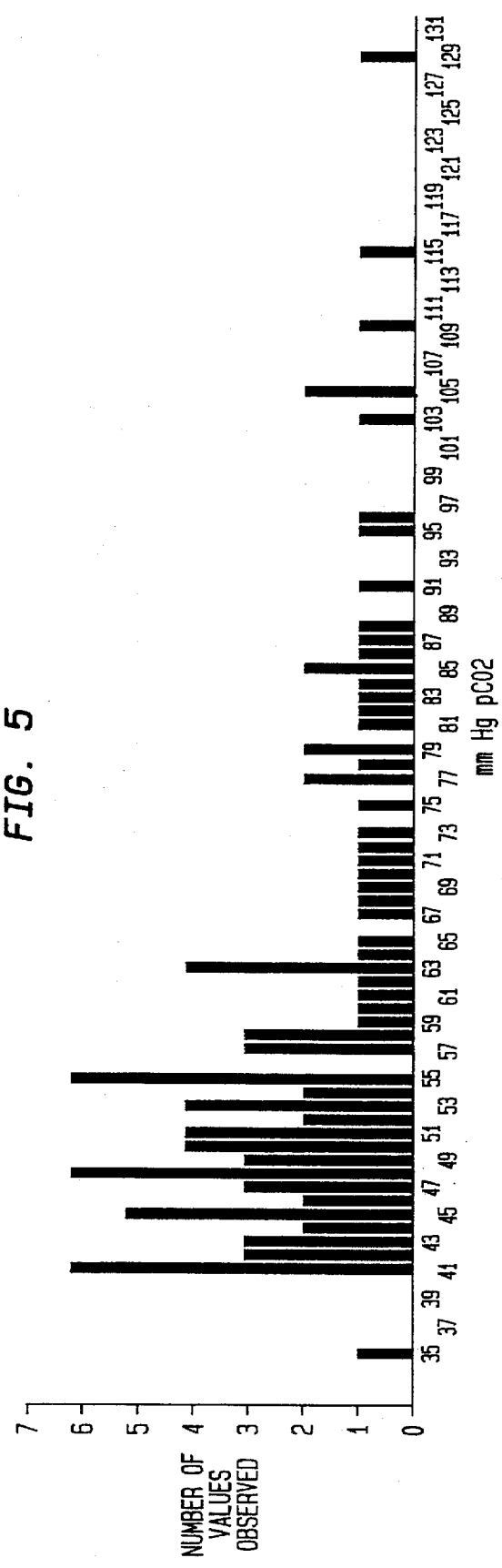
FIG. 5 is a bar graph display of the range of concentrations of $CO_2$ in one hundred and four samples of urine (same as used in FIG. 4) depicting the variations possible four minutes after the sample is given.
Figure 6:
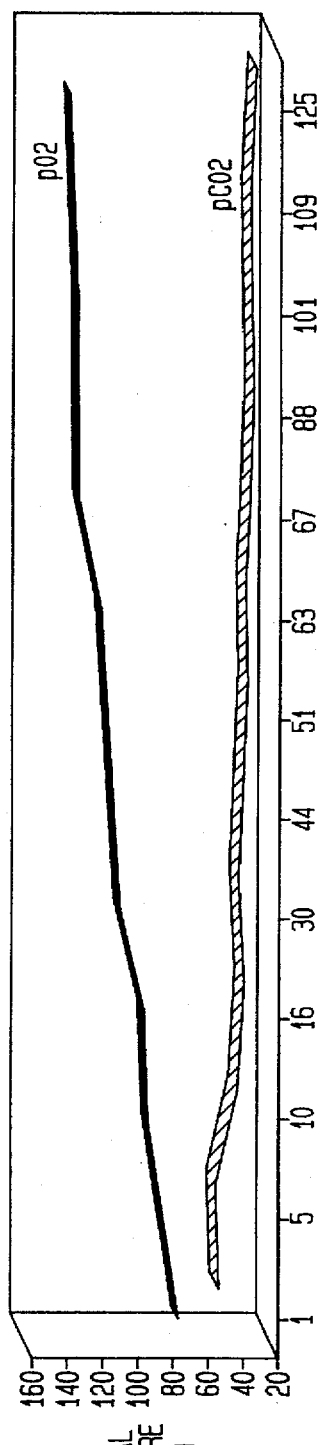
Figure 7:
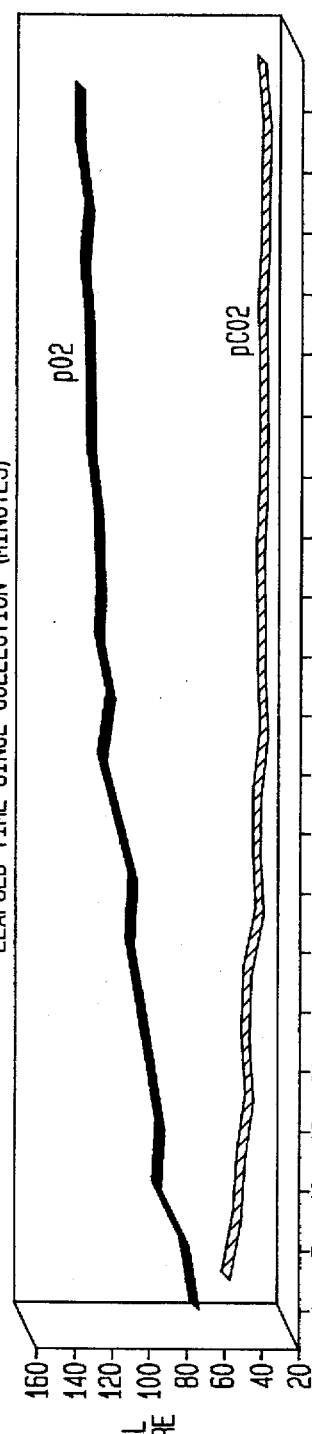
Figure 8:
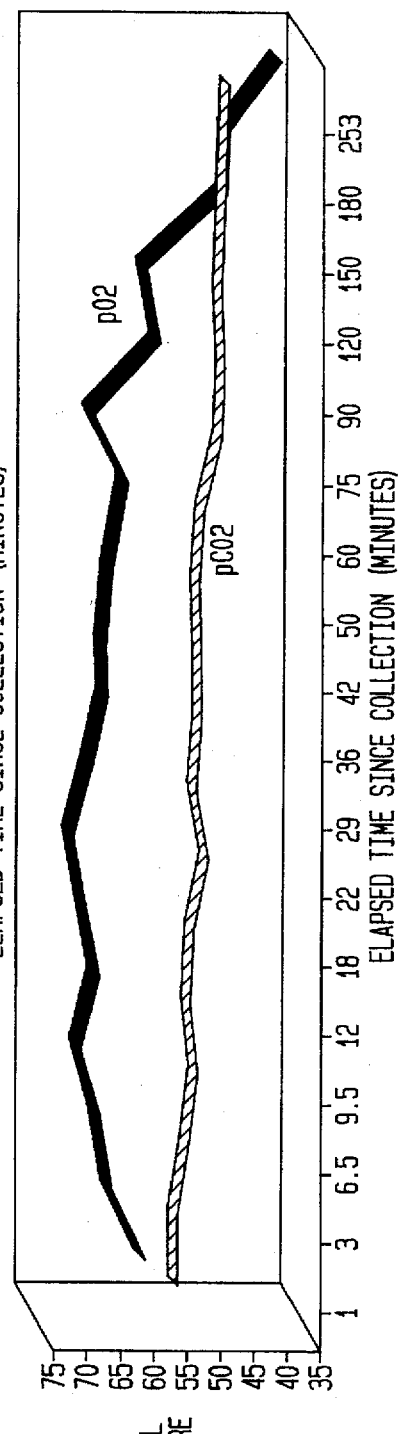
Figure 9:
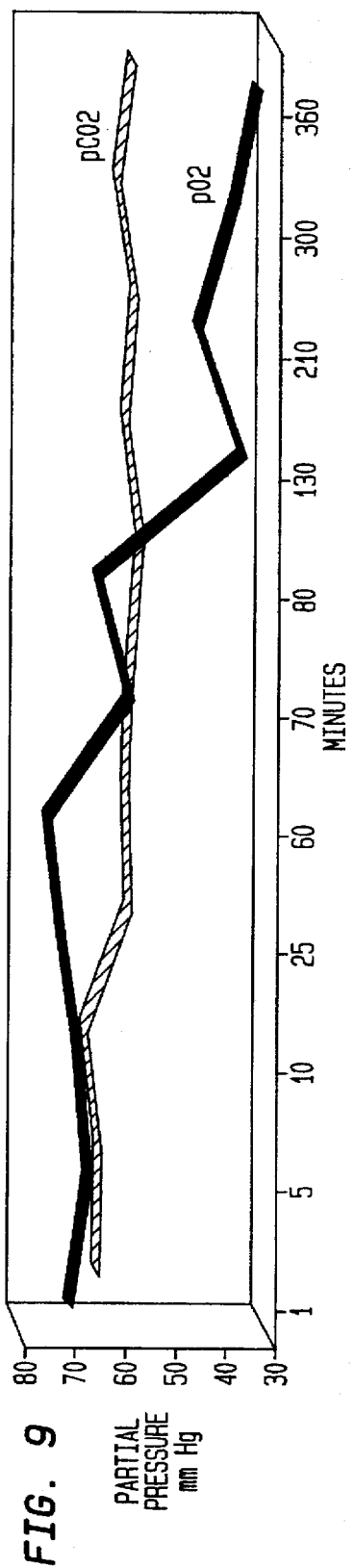
Figure 10:
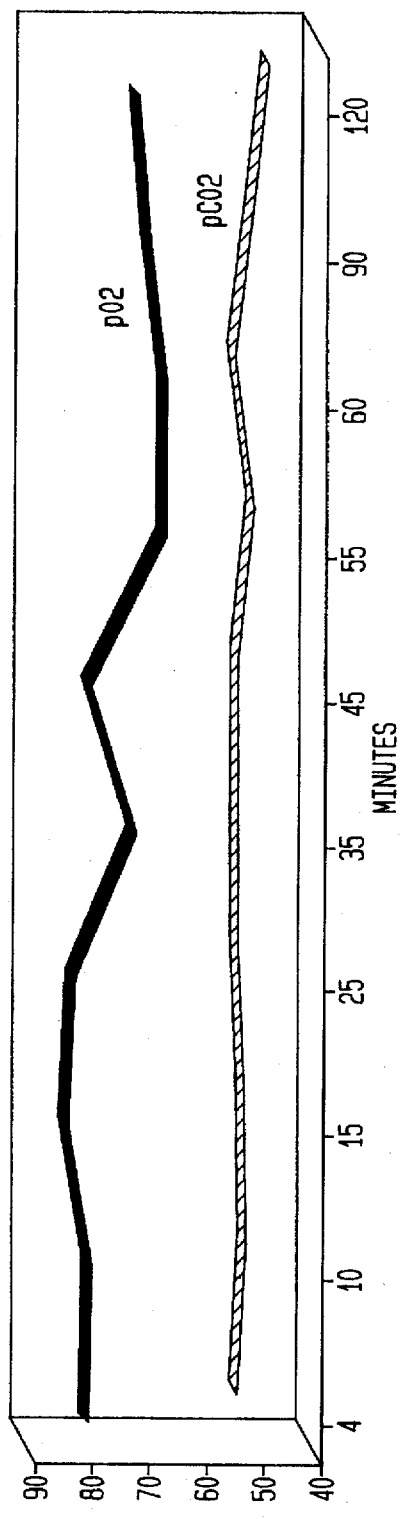
Figure 11:
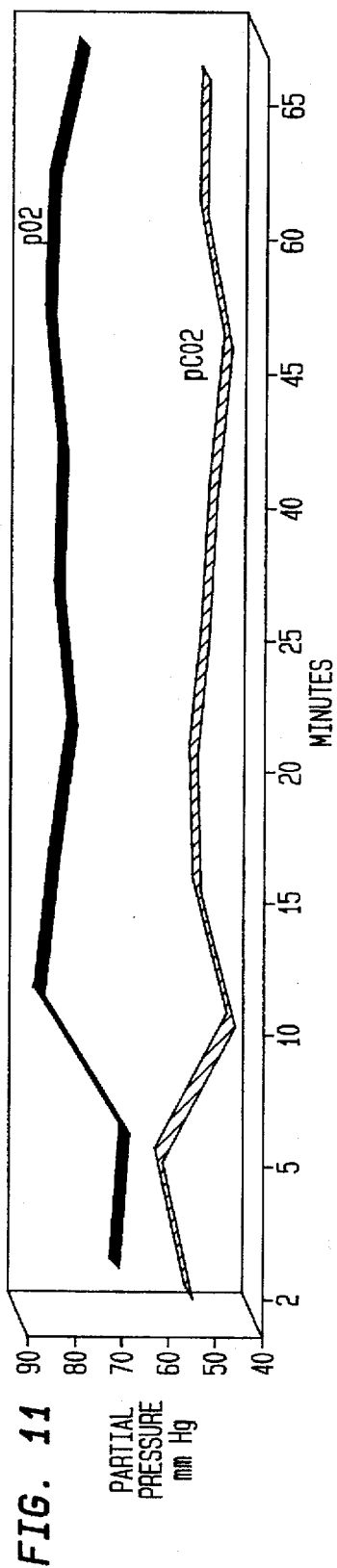

Turning our attention to FIGS. 4 and 5, they show that the non-parametric 95 per cent reference range of the partial pressure of $CO_2$ dissolved in urine four minutes after a sample is given is between 40 and 112 mmHg. The non-parametric 95 per cent reference range for $O_2$ for the same conditions is between 37 and 100 mmHg. Since $CO_2$ dissolved in urine is steadily decreasing, this range is important in the detection of bogus samples. Ordinary tap water, for example, will have a low concentration of dissolved $CO_2$ somewhere in the range of 5 mmHg partial pressure. A sample in this low range of $CO_2$ concentration would be rejected as being either bogus or very old.

A sample of carbonated soda was tested and it revealed excessively high levels of $CO_2$ in solution. All tested samples contained concentrations over 515 mmHg in solution.

The distinction between bogus and authentic specimens can therefore be automated quite simply utilizing a computer algorithm to compare measured values against an acceptable range. A sample is acceptable if the partial pressure is $\geq 33$ mmHg but not $\geq 121$ mmHg of $O_2$ in solution. A similar algorithm can be established for concentrations of $CO_2$ in solution which are acceptable if $\geq 40$ mmHg but not $\geq 115$ mmHg. In this manner samples can be automatically screened, and rejected or accepted based upon absolute values of gas concentrations.

The rate of change in the levels of concentration of $O_2$ over time taken in combination with measurements of $CO_2$, lend themselves to very accurate timing of the aging process of urine. The rates of change in concentrations of $CO_2$ can be used for intervals from 0 to 3 hours; after the first hour as can be observed from FIGS. 1-3, the concentration levels of $O_2$ begin to change more rapidly, suggesting that aging tests should be combined with the levels of concentration of $O_2$ gas in solution. Small changes over time in these concentrations suggest that the sample is from 0 to 60 minutes old. Large changes suggest aging intervals greater than 60 minutes old. Accordingly, when the combined measurements are utilized together, more accurate indications are available.

For diagnostic tests requiring the absolute value of $O_2$ or $CO_2$ in the urine, the process of aging, i.e. the change in concentrations of these components, $O_2$ and $CO_2$ over time, should be halted or stabilized. To avoid equilibration with the atmosphere and thus eliminate the need to measure $PO_2$ and $PCO_2$ immediately after voiding, a specimen should be collected in a testing apparatus such as an evacuated container or, once placed in a container, the specimen should be covered with a gas impermeable material, such as a layer of mineral oil or the container should be air-tight when closed.

Measurements of available $O_2$ and $CO_2$ in a specimen can be measured with $O_2$ and $CO_2$ sensitive electrodes, such as the OXEL-1 electrode sold by World Precision Instruments, Inc. of Sarasota, Fla. In a sealed specimen sample such electrodes can be pre-positioned to provide readings while the integrity of the seal is preserved. Alternatively, solid phase reagent assays that use as a rate-limiting step the availability of either $O_2$ and $CO_2$ can be employed to measure concentration levels. Some examples of these include:

(1) enzymatic reactions based upon chlorophyll for which the concentration of $CO_2$ determines the amount of reaction product generated, here $O_2$;

(2) oxidative reactions, such as the enzyme-based reactions used in glucose and energy metabolism M, in which glucose, NADPH, fructose or $CO_2$ can be measured to indicate the amount of $O_2$ present; and (3) carbonic anhydrase.

I claim:

1. A method for identifying a bogus urine specimen, including the steps of:

procuring a urine specimen;

measuring the concentration of at least one naturally occurring gas dissolved in said urine specimen, wherein said at least one gas is selected from a group consisting of oxygen and carbon dioxide;

determining the elapsed period of time between procuring said urine specimen and said step of measuring the concentration of at least one gas; and comparing the concentration of said at least one gas against a pre-determined range of reference measurements for said elapsed period of time to determine whether the specimen is bogus.

2. The method recited in claim 1, wherein said at least one naturally occurring gas is oxygen, said elapsed period of time is between 0 and 3 hours, and said predetermined range is between 33 mmHg and 121 mmHg.

3. The method recited in claim 1, wherein said at least one naturally occurring gas is oxygen, said elapsed period of time is between 0 and three hours, and said predetermined range is between 40 mmHg and 115 mmHg.

4. The method recited in claim 1, wherein said at least one naturally occurring gas is carbon dioxide and said predetermined range of reference measurements is above 40 mmHg.

5. The method recited in claim 1, wherein said at least one naturally occurring gas is carbon dioxide and said predetermined range of reference measurements is below 112 mmHg.

6. The method recited in claim 1, wherein said at least one naturally occurring gas includes both oxygen and carbon dioxide and said method further includes the step of determining the age of said urine specimen by comparing the concentrations of oxygen and carbon dioxide in said urine specimen with said pre-determined acceptable range of measurements.

7. A method for diagnostic evaluation of a medical disorder utilizing urine specimens from a subject under examination comprising the steps of:

acquiring a sample of urine;

measuring the partial pressure of oxygen in solution in said urine to obtain a first measured value;

determining a first elapsed period of time between acquiring said urine specimen and said step of measuring the partial pressure of oxygen;

measuring the partial pressure of carbon dioxide in solution in said urine to obtain a second measured value;

determining a second elapsed period of time between acquiring said urine specimen and said step of measuring the partial pressure of carbon dioxide; and comparing said first measured value against a pre-determined range of normal oxygen values for said first elapsed period of time and comparing said second measured value against a pre-determined range of normal carbon dioxide values for said second elapsed period of time to determine an abnormal condition, thereby providing a diagnostic evaluation of a potential disorder.

8. A method for verifying the integrity of a urine specimen in a liquid state, comprising the steps of:

procuring said urine specimen;

taking an initial partial pressure measurement of at least one naturally occurring gas dissolved in said specimen at a first time interval;

taking a subsequent partial pressure measurement of said at least one naturally occurring gas dissolved in said specimen at a later second time interval;

comparing said initial partial pressure measurement and said subsequent partial pressure measurement to determine a rate of change between said first time interval and said second time interval; and determining the elapsed period of time between procuring said urine specimen and said first time interval;

comparing said rate of change over time with a predetermined acceptable range based upon said elapsed period of time to verify authenticity.

9. The method recited in claim 8, wherein at least one naturally occurring gas is oxygen, and said rate of change over time shows an increase in oxygen over time.

10. The method recited in claim 8 wherein at least one naturally occurring gas is carbon dioxide and said rate of change over time shows a decrease in carbon dioxide over time.

* * * * *